United States Patent
Yates et al.

(10) Patent No.: US 10,272,108 B2
(45) Date of Patent: *Apr. 30, 2019

(54) ANTIMICROBIAL SILVER HYDROGEL COMPOSITION FOR THE TREATMENT OF BURNS AND WOUNDS

(71) Applicant: CelaCare Technologies, Inc., Dallas, TX (US)

(72) Inventors: Kenneth M Yates, Keller, TX (US); Celia A Proctor, Lead Hill, AR (US); Dan H Atchley, Searcy, AR (US)

(73) Assignee: CELACARE TECHNOLOGIES, LLC, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/095,839

(22) Filed: Apr. 11, 2016

(65) Prior Publication Data

US 2016/0243164 A1    Aug. 25, 2016

Related U.S. Application Data

(63) Continuation-in-part of application No. 13/101,724, filed on May 5, 2011, now Pat. No. 9,327,029.

(51) Int. Cl.
| | |
|---|---|
| *A61K 33/38* | (2006.01) |
| *A61P 17/02* | (2006.01) |
| *A61P 31/10* | (2006.01) |
| *A61P 31/12* | (2006.01) |
| *A61K 36/886* | (2006.01) |
| *A61P 31/04* | (2006.01) |
| *A61K 31/715* | (2006.01) |
| *A61K 9/00* | (2006.01) |
| *A61K 47/10* | (2017.01) |
| *A61K 47/26* | (2006.01) |
| *A61K 47/32* | (2006.01) |
| *A61K 47/38* | (2006.01) |
| *A61K 31/4166* | (2006.01) |
| *A61K 9/06* | (2006.01) |

(52) U.S. Cl.
CPC ............ *A61K 33/38* (2013.01); *A61K 9/0014* (2013.01); *A61K 9/06* (2013.01); *A61K 31/4166* (2013.01); *A61K 31/715* (2013.01); *A61K 36/886* (2013.01); *A61K 47/10* (2013.01); *A61K 47/26* (2013.01); *A61K 47/32* (2013.01); *A61K 47/38* (2013.01)

(58) Field of Classification Search
CPC ..................................................... A61K 23/00
See application file for complete search history.

(56) References Cited

U.S. PATENT DOCUMENTS

| | | | |
|---|---|---|---|
| 5,939,427 A | 8/1999 | Kagayama et al. | |
| 6,071,541 A | 6/2000 | Murad | |
| 6,294,186 B1 | 9/2001 | Beerse et al. | |
| 7,511,007 B2 | 3/2009 | Tichy et al. | |
| 2002/0151521 A1 | 10/2002 | Burke et al. | |
| 2006/0089342 A1 | 4/2006 | Gavin et al. | |
| 2008/0014247 A1* | 1/2008 | Lu ...................... A61K 9/0014 | |
| | | | 424/436 |
| 2009/0263500 A1 | 10/2009 | Gorinshteyn | |
| 2010/0255130 A1 | 10/2010 | Debaun et al. | |
| 2012/0208877 A1 | 8/2012 | Raffy | |

FOREIGN PATENT DOCUMENTS

| | | |
|---|---|---|
| CH | 699182 A1 | 1/2010 |
| GB | 2462678 A | 2/2010 |
| WO | 2005000324 A2 | 1/2005 |
| WO | 2006074117 A2 | 7/2006 |
| WO | 2006093792 A1 | 9/2006 |

OTHER PUBLICATIONS

Atiyeh, et al., "Effect of Silver on Burn Would Infection Control and Healing: Review of the Literature", Burns, 2007, vol. 33. pp. 139-148.
Davis et al., "Cosmeceuticals and Natural Products" Would Healing; Clinics in Dermatology, 2009, vol. 27, No. 5, pp. 502-506.
Heggers et al., "Wound Healing Effects of Aloe Gel and Other Topical Antibacterial Agents on Rat Skin", Phytotherapy Research, 1995, vol. 9, No. 6, pp. 455-457.
The International Search Report and Written Opinion issued by the European Patent Office dated Aug. 7, 2012 for PCT application No. PCT/US2012/036384.
Senamed, Oct. 21, 2008, retrived at: http//web/archive.org/web/20081021090614/http:/www.sebamed.com/265.html.
Talmadge et al. "Fractionation of *Aloe vera* L. Inner Gel, Purification and Molecular Profiling of Activity", International Immunopharmacology, 2004, vol. 4, pp. 1757-1773.
Zhang et al. "Activation of a Mouse Macrophage Cell Line by Acemannan: The Major Carbohydrate Fraction from Aloe Vera Gel", Immunopharmacology, 1996, vol. 35, pp. 119-128.
Karaca et al. "Nitric Oxide Production by Chicken Macrophages Activated by Acemannan, A Complex Cabohydrate Extracted from Aloe Vera", Int. J. Immunopharmacology, 1995, vol. 17, No. 3, pp. 183-188.

(Continued)

*Primary Examiner* — David J Blanchard
*Assistant Examiner* — Sarah Alawadi
(74) *Attorney, Agent, or Firm* — Jackson Walker LLP

(57) ABSTRACT

An antimicrobial therapeutic hydrogel composition comprises a pharmaceutical and/or medical grade silver salt, and an Aloe vera gel or extract. The composition could also include stabilizing agents, a non-ionic surfactant, polyol, and hydrophilic hygroscopic polymers. The resulting product has potent antimicrobial activity against bacteria, protozoa, fungi and viruses. The antimicrobial therapeutic composition can serve as a treatment for burns and as a wound/lesion dressing that either donates or receives moisture to provide a physiologic environment for accelerated wound healing and the relief of pain.

28 Claims, No Drawings

(56) References Cited

OTHER PUBLICATIONS

Jittapiromsak et al., "Acemannan, an Extracted Product from Aloe Vera, Stimulates Dental Pulp Cell Proliferation, Differentiation, Mineralization, and Dentin Formation", Tissue Engineering: Part A, 2010, vol. 16, No. 6, pp. 1997-2007.

Jettanacheawchankit, Acemannan Stimulates Gingival Fibroblast Proliferation; Expressions of Keratinocyte Growth Factor-1, Vascular Endothelial Growth Factor, and Type I Collagen; and Wound Healing; J. Pharmacol Science, 109, 2009, pp. 525-531.

Poon, V., et al; In Vitro Cytotoxity of Silver: Implication for Clinical Wound Care; Burns 30, 2004, pp. 140-147.

Lowe, D.G., et al: Silver Deposition in the Cervix After Application of Silver Nitrate as a Cauterising Agent; J. Clinical Pathology, 41, 1988; pp. 871-874.

Liedberg, H., et al; Assessment of Silver-Coated Urinary Catheter Toxicity by Cell Culture; Urol. Res. 17, 1989, pp. 359-360.

Baldi, C., et al: Effects of Silver in Isolated Rat Hepatocytes; Toxicology Letters, 41, 1988, pp. 261-268.

Hussain, Saber, et al: Cysteine Protects Na,K-ATPase and Isolated Human Lymphocytes From Silver Toxicity; Biochemical and Biophysical Research Communications, vol. 189, No. 3, Dec. 30, 1993, pp. 1444-1449.

Klasen, H.J.; A Historical Review of the Use of Silver in the Treatment of Burns. II. Renewed Interest for Silver; Burns 26, 2000, pp. 131-138.

Burrell, Robert E.: A Scientific Perspective on the Use of Topical Silver Preparations; Ostomy Wound Manage, vol. 49, 5A Supplement, 2003.

Jackson, W.F., et al: Toxic Effects of Silver-Silver Chloride Electrodes on Vascular Smooth Muscle; Circulation Research Journal of the American Heart Association, 53, 183, pp. 105-108.

Lex M. Cowsert. Biological Activities of Acemannan. Dec. 8, 2010.

European Patent Office, Response to Office Action, European Application No. 12721109.2, dated Jan. 20, 2015.

The Communication pursuant to Article 94(3) EPC issued by the European Patent Office dated Jun. 7, 2016 for the corresponding European application No. 12721108.2.

Hamman, "Composition and Applications of Aloe vera Leaf Gel", Molecules, 2008, vol. 13, No. 8, pp. 1599-1616.

The Reply in response to the Communication pursuant to Article 94(3) EPC dated Jun. 7, 2016, as filed with the European Patent Office on Nov. 22, 2016 for the corresponding European application No. 12721109.2.

* cited by examiner

ANTIMICROBIAL SILVER HYDROGEL COMPOSITION FOR THE TREATMENT OF BURNS AND WOUNDS

RELATED APPLICATIONS

This application is a continuation-in-part of U.S. patent application Ser. No. 13/101,724, filed on May 5, 2011, entitled "Antimicrobial Silver Hydrogel Composition for the Treatment of Burns and Wounds," which is hereby incorporated by reference for all purposes as if set forth herein in its entirety.

BACKGROUND

One aspect of the present invention relates to a therapeutic hydrogel composition where a stabilized form of an antimicrobial complex silver salt is incorporated and further stabilized within a matrix of different polymers and other excipients to form an antimicrobial dressing with properties of pain relief and optimal and accelerated wound healing by creating a dynamic physiological environment suitable for treatment of burns and wounds/lesions.

Bacteria, fungi, and viruses present significant challenges to wound healing, and increase morbidity and mortality. Subsequent wound complications may range from delayed healing, to local and widespread infections, and possible death. Treatment of wounds/lesions such as, but not limited to, second and third degree burns, pressure ulcers, diabetic ulcers, surgical wounds, and various skin abrasions can be difficult to treat in part due to possible infections from microorganisms; and the rise in incidence of superinfections and multiple drug resistant microorganisms.

Infected wounds disrupt the three main phases in wound healing by prolonging the initial inflammatory phase ordinarily lasting one to five days. Once prolonged the second phase known as the proliferative phase generally lasting three to four weeks, and the final phase of epithelialization and tissue remodeling cannot follow the normal wound healing continuum.

Current chemotherapeutic antimicrobial agents have been used topically and systemically for treating and preventing infections in wounds for many years. The current therapy of choice for wound infections is the use of systemic antimicrobials. Systemic use of antimicrobials creates several potential problems including side effects and poor bioavailability to the wound site. This approach is also problematic with the rise in incidence of superinfections with organisms such as Enterobacteriaceae, *Pseudomonas*, and *Candida* as well as microbial drug resistance leading to difficult to treat infections such as MRSA (Methicillin Resistant *Staphylococcus aureus*) and vancomycin-resistant enterococcus (VRE).

The use of topical antimicrobial wound dressings have become significantly more important over the last decade especially in immunocompromised patients such as older adults and patients with diabetes, HIV, burns and those having surgical wounds. These patients are at higher risk for chronic wound infections with prolonged healing times due to the presence of bacteria at greater than $10^5$ to $10^6$ colony forming units/g. This burden of bacteria prolongs the inflammatory phase of wound healing and inhibits the proliferative phase due to increase in protease levels. Consequently, the third phase of wound healing, the epithelialization and tissue remodeling phase, cannot proceed if the initial phases do not advance appropriately.

One of the potential issues faced with chronic wounds is the prolongation of the initial or inflammatory phase due to infection as previously described. Bacteria growth can also lead to changes in metabolic demand with increased levels of protease enzymes. This problem is especially pronounced in diabetic wounds where abnormal metabolic functions are already present. In addition, increased levels of extracellular glucose in diabetic wounds provide an excellent growth media for organisms. As previously mentioned, bioburden microorganism densities greater than $10^5$-$10^6$ colony forming units/g are considered a threshold for delayed wound healing and pathology. These wounds have increased exudate, odor, pain and change in color and texture of the wounded tissue. Even in the absence of these signs, infection should be considered if a wound fails to heal in a timely manner. Delay in wound healing may also be due to immune incompetency or poor circulation that is not uncommon in older adults. Wounds such as venous stasis ulcers and decubital ulcers are excellent examples of these types of wounds.

Due to increases in hospital acquired infections with highly multi-drug-resistant bacteria and fungi, surgical wounds are also at risk for infection that can lead to dehiscence or serious delays in healing.

Another health burden seen worldwide, primarily affecting children and young healthy adults are burns. The American Burn Association reported 450,000 patients were treated for burns in hospital emergency departments, hospital outpatient clinics, freestanding urgent care centers or private physician offices. Heat burns and scalds serve as the primary source of injury occurring around the house, with young children at highest risk. Burns are classified as first, second or third degree injuries based on the depth of the injury, with a third degree burn being the most severe resulting in a full thickness wound, i.e. extending into the dermis or subcutaneous tissue. Depending on the severity of the burn, the individual is susceptible to infection. Regardless of the severity the wound is painful. Inflammatory agents are released at the burn site causing swelling and pain at the site of injury. As previously mentioned, secondary bacterial and fungal infections are problematic and delay wound healing or cause more serious consequences, possibly death. The most common organisms that infect burn wounds are *Staphylococcus aureus*, Group A *Streptococcus, Pseudomonas aeruginosa*, and *Candida*. Each of these organisms have the potential to develop multi-drug resistance and the potential to be life threatening.

Cutaneous viral infections can create painful skin lesions that are difficult to heal or take a prolonged time. It is not uncommon for HIV immunosuppressed patients to experience skin lesions from viral infections. The most common virus affecting these patients is Herpes simplex virus (HSV). Varicella zoster/Herpes zoster virus (chicken pox/shingles) is also problematic in HIV patients but may also affect older adults as well as other immunocompromised individuals. Herpes labialis (cold sores) also caused by HSV is also a common cutaneous viral infection that creates painful lesions at the muco-cutaneous junction associated with the lips. These lesions occur in all age groups but especially with individuals under stress and reduced immunocompetence. Many other viruses can impact the skin and cause different types of lesions such as Human papilloma virus (HPV), Poxvirus and Cytomegalovirus (CMV).

Multiple therapeutic approaches have been utilized to deal with healing issues associated with wound infections and burns. It is now widely accepted that moist wound healing is critical for proper healing and acceleration of the process.

Combinations of primary dressings, such as hydrogels, or use of different antimicrobial dressings have been employed to help address these issues. The most common topical antibiotics used are mupirocin, clindamycin, erythromycin, gentamicin and the combination of bacitracin, neomycin, and polymyxin B sulfate. These products have limitations related to multi-drug resistance, as well as their formulations having the potential to delay healing. Tolnaftate, nystatin and amphotericin B have commonly been used as topical antifungals. These agents also have the potential to delay healing or demonstrate adverse events. Acyclovir ointment is the most common topical drug for treating HSV; however as an ointment it doesn't provide wound conditions for optimal healing. Additionally, increased resistance to acyclovir is a growing concern. Other topical antiviral products utilized, such as, penciclovir cream and docosanol cream, have shown similar problems in regards to their impact on the wound environment having little or no effect on healing times, other than their antimicrobial effect.

Multiple approaches to treatment are recommended dependent upon the extent and severity of burns. One percent silver sulfadiazine cream is the most commonly used topical antimicrobial treatment for burns. A limitation of this product is its hydrophobic base that presents as a significant problem in removal from the site of injury prior to redressing. Removal can result in significant pain for the patient. Another current treatment of choice, mafenide has a limitation of altering acid-base balance of the wound negatively impacting rate of healing. Newer silver containing products have been introduced; such as a microlattice synthetic hydrogel product that attempts to address some of the associated problems of semisolid emulsion (creams) based products.

The purpose of the present invention is to impact a burn or wound/lesion by decreasing bioburden, pain, healing time, morbidity, and mortality.

SUMMARY

The design of one aspect of the present invention addresses the current issues that exist with presently available products. It combines potent antimicrobial agents that offer limited opportunity for development of microorganism resistance with other physiological acceptable key constituents that: a) treat and/or prevent wound bioburden b) aid in maintaining an appropriate wound environment by either receiving or donating moisture, thereby enhancing immune function thus accelerating healing, and c) aid in pain management to provide improved patient comfort.

It is therefore one embodiment of the invention to provide a topical antimicrobial burn and wound composition that has broad-spectrum activity against bacteria, protozoa, fungi and virus infections that result in or the result of a wound/lesion.

It is a second embodiment of this invention to provide a therapeutic topical composition that has more potent broad-spectrum antimicrobial activity than silver salts alone.

It is a third embodiment of this invention to provide a therapeutic composition that creates a physiologic environment for optimal and/or accelerated wound/lesion healing including burns.

It is a fourth embodiment of this invention to provide a therapeutic composition that will relieve pain when applied to a wound/lesion including burns.

It is a fifth embodiment of this invention to provide a therapeutic composition that can function as a wound/lesion dressing that can donate or receive moisture to maintain an appropriate moisture balance for physiological healing of the wound/lesion including burns.

DETAILED DESCRIPTION OF THE PREFERRED EMBODIMENTS

One aspect of the current invention comprises a composition containing a pharmaceutical or medical grade silver salt, and Aloe vera gel or Aloe vera extract containing acemannan. It can also contain non-ionic water-soluble polymer thickener, moisturizers and humectants, stabilizers, skin protectant, and allantoin for their varied wound healing properties.

A silver salt serves as the primary antimicrobial agent in the composition. It is well accepted that it is the ionic form of silver that is antimicrobial. The principle mechanism of action results from ionic silver binding to microbial proteins causing structural changes in cell walls and intracellular and nuclear membranes. In addition, it has been shown that silver binds to DNA and RNA, denatures nucleotides and thereby inhibits replication. Silver salts used in the current invention can be in the hydrous or anhydrous form. As used herein, the term "anhydrous" means essentially free of water, i.e. less than 10% retained water. The term does not mean totally free of water. As used herein, the term "hydrous" would mean containing water greater than 10% and would include a concentrate. Examples of silver salts that could be used in the present invention include, but are not limited to, silver nitrate, silver dihydrogen citrate, silver citrate, silver chloride, silver benzoate, silver acetate, silver galacturonate, and silver glucuronate. The concentration of ionic silver as a salt formulated in the first embodiment of the present invention can range from 0.01 ppm to 1000 ppm, a second embodiment with a concentration of 1-100 ppm and a third embodiment with a concentration of 5-50 ppm. These concentrations of ionic silver in a topical formulation are not considered toxic. It has been demonstrated and is noteworthy that when a wound dressing containing 85 mg 100 $cm^{-1}$ of ionic silver was applied to the skin of chronic ulcer patients for four weeks, systemic blood levels of silver was not significantly different from controls.

The inner clear mucilage gel of Aloe vera, referred to as Aloe vera gel, has been used for centuries to treat and manage wounds. Aloe vera gel is separated from the rind of the Aloe vera plant by filleting an aloe leaf, separating the inner gel from the outer leaf rind and separating it from the yellow sap contained within the rind. The inner gel is then homogenized and available for use or further processing either as a concentrate by removal of water or more extensive processing to create an extract. The Aloe vera gel contains a variety of chemical substances with a large molecular weight complex carbohydrate, identified and given the United States Adopted Name, acemannan. Fundamentally, acemannan the high molecular weight carbohydrate polymer of the gel can be separated either by alcohol precipitation, column purification or ultra-filtration. Aloe vera gel and its principle extract including acemannan process for preparation and its uses have been described in U.S. Pat. Nos. 4,735,935, 4,851,224, 4,957,907, 4,959,214, 4,917,890, 4,966,892, 5,106,616, 5,118,673, 5,308,838, 5,441,943, 5,703,060, 5,760,102 and 5,902,796. The entire contents of each patent are hereby incorporated by reference. Multiple properties have been attributed to this compound but the most predominant has been its immunomodulation function. Included as part of the immunomodulation property is the ability to stimulate release of primary growth factors necessary for optimal and accelerated wound healing. There is also some evidence that acemannan may interfere with adherence of bacteria to epithelia cells. In addition to its immune modulation activities it has also been shown to have anti-inflammatory properties and aid in the control of pain. An Aloe vera cream was compared to silver sulfadiazine in second-degree burn patients and demonstrated significant improvement in re-epithelialization times as compared to silver sulfadiazine. The use of an aloe extract acemannan gel as a component of the present invention provides multiple attributes for accelerated healing, inflammation and pain control. Aloe vera gel or its extract, bulk acetylated mannans from Aloe vera (acemannan) have not been shown to be toxic or cause allergic reaction at the concentrations used in the present invention and any one of these products would be suitable for use. An anhydrous form of Aloe vera gel extract was utilized in the present invention. The concentration of anhydrous Aloe vera gel extract acemannan in the first embodiment of the present invention can range from 0.01-1.0 w/w %, in the second embodiment from 0.05-0.3 w/w %, and a third embodiment from 0.075-0.2 w/w %.

Tetraacetic acid compounds can be used in the present invention as a stabilizer for silver salt. Stabilizing chelating agents or tetra acetic acid chelating compounds include, but are not limited to, ethylenediaminetetraacetic acid (EDTA), 1,2-bis(o-aminophenoxy) ethane-N,N,N',N'-tetraacetic (BAPTA), 1,4,7,10-tetraazacyclododecane-1,4,7,10-tetraacetic acid (DOTA), and ethylene glycol tetraacetic acid (EGTA), and mixtures thereof. EDTA may be used as, but is not limited to, its salt form, including either tetrasodium ethylenediaminetetraacetic acid (EDTA Tetrasodium) or disodium ethylenediaminetetraacetic acid (disodium EDTA). All of the tetraacetic acid compounds listed above may be used in their salt forms, including but not limited to their sodium salt forms. Topical exposure of Disodium EDTA for 4 hours in a human patch test showed no reactivity thus it is an excellent stabilizer for topical products. In addition, it has been shown that tetraacetic acid compounds in conjunction with a silver salt, more specifically silver nitrate, significantly increased the antibacterial action of the silver. The concentration of stabilizing chelating agent in preferred embodiments of the current invention can range from 0.01-5.0 w/w %, in a second embodiment from 0.1-2.5 w/w %, and in a third embodiment from 0.25-1.0 w/w %.

A second stabilizer and dispersant that can be included in the composition is polyvinylpyrrolidone (PVP). PVP has been used as a dispersant for Aloe vera gel, gel concentrates and gel extracts as well as for silver salt antimicrobial matrix products. The concentration of PVP in the first embodiment of the present invention can range from 0.1-5.0 w/w %, in a second embodiment from 0.5-2.5 w/w %, and in a third embodiment from 1.0-2.0 w/w %.

Polysorbates are sorbitan esters, also known as Tweens, serve as non-ionic surfactants. These groups of compounds known as polyoxyethylene derivatives are fatty acid esters of sorbitol copolymerized with ethylene oxide. It has been demonstrated that polysorbate 80 increases *Pseudomonas aeruginosa* cell permeability increasing cell leakage. However, the effect on growth rate of the bacteria was not impacted. Polysorbate surfactants are currently used with multiple antimicrobial drugs to increase their pharmacologic activity. In the current invention polysorbate can be used as a surfactant and microbial membrane permeability enhancer. Polysorbate compounds that can be chosen and used for the present invention include, but are not limited to, laurate ester; palmitate ester; mixture of stearate and palmitate esters and oleate ester. The concentration of polysorbate in the first embodiment of the present invention can range from 0.01-0.2 w/w %, in the second embodiment from 0.05-0.175 w/w %, and a third embodiment from 0.075-0.125 w/w %.

Allantoin, (2,5-Dioxo-4-imidazolidinyl) urea, is the diureide of glyoxylic acid. Allantoin has been used in wound healing preparations for many years and has been approved as a skin protectant by the United States Food and Drug Administration. It currently is considered safe for use as an oral wound healing agent and in addition has a reported use in the treatment of burns as the silver salt. The concentration of allantoin in the first embodiment of the present invention can range from 0.0001-2.0 w/w %, a second embodiment from 0.1-1.5 w/w %, and a third embodiment from 0.5-1.0 w/w %.

Humectants are hygroscopic substances that have the ability to absorb or donate moisture to a wound. If a wound is dry, a humectant substance will absorb moisture from the environment and help maintain a moist wound environment for more optimal healing. If a wound is producing more serous fluid then humectant substances can aid in absorption of the extra fluid, helping maintain a more appropriate wound environment. The current invention utilizes three different humectants in the composition; propylene glycol, panthenol and glycerin. In addition to having humectant and moisturizing properties, panthenol is a precursor to vitamin B5, pantothenic acid, and is essential for synthesis of keratinocyte growth factor and fibroblast proliferation critical to optimal and accelerated wound healing. Glycerin or glycerol is the principle humectant in the current invention. Glycerin is very hygroscopic making it ideal in the absorption or donation of moisture. The humectants as part of the compositions separate the current invention from current art for hydrogel dressings. The concentration of propylene glycol in the first embodiment of the present invention can range from 0.01-1.0 w/w %, a second embodiment from 0.05-0.5 w/w %, and a third embodiment from 0.15-0.3 w/w %. The concentration of panthenol in the first embodiment of the present invention can range from 0.1-3.0 w/w %, a second embodiment from 0.5-2.0 w/w %, and a third embodiment from 0.75-1.5 w/w %. The concentration of glycerin in the first embodiment of the present invention can range from 1-25 w/w %, a second embodiment from 5-20 w/w %, and a third embodiment from 10-15 w/w %.

Nonionic water-soluble polymers have been used for many years as components of therapeutic products as binders, stabilizers, suspending agents and thickeners. These polymers are generally non-irritating and non-allergenic. Examples of these polymers that are acceptable for use in the present invention include, but are not limited to, hydroxyethylcellulose, carboxymethylcellulose, hydroxypropylcellulose, hypromellose, ethylcellulose, or their derivatives. The concentration in the first embodiment of the current invention can range from 0.01-5.0 w/w %, a second embodiment from 0.25-2.5 w/w %, and a third embodiment from 0.5-1.5 w/w %.

A buffering agent is utilized in the present invention to achieve a pH appropriate for optimal wound healing. Buffers suitable for use include, but are not limited to, sodium hydroxide (NaOH), triethanolamine and tromethamine. The desired pH in the first embodiment for the present invention can range from 4-7.4.

The Examples of compositions that follow were compounded by adding ingredients except glycerin to pharmaceutical grade water (USP Purified Water) at a temperature of 35 to 50° C. and mixing using a rotary mixer at speeds from 400 to 1500 rpm to allow for sufficient agitation to solubilize and disperse the ingredients. Dependent on the volume and mixer used, mixer speeds can vary. Total time for appropriate mixing varied dependent on materials selected to allow for ingredient solubilization and dispersion but in general, mixing was carried out for up to 4 hours. The last step in the formulation process was the addition of glycerin while cooling, mixing for 30 minutes to arrive at the final antimicrobial therapeutic hydrogel composition. Ingredients are commercially available.

Example 1

An embodiment of the present invention was compounded as described to determine materials compatibility and range of material usage.

Silver citrate salt 1.5 ppm, Aloe vera acemannan 0.15 w/w %, hydroxyethylcellulose 1 w/w %, polyvinylpyrrolidone 1.5 w/w %, disodium EDTA 0.5 w/w %, DL-panthenol 1 w/w %, propylene glycol 0.2 w/w %, glycerin 15 w/w %, purified water 79.6%, buffered with 0.1 M sodium hydroxide to pH 6.5.

Example 2

An embodiment of the present invention was compounded as described to determine materials compatibility and range of material usage.

Silver citrate salt 15 ppm, Aloe vera acemannan 0.15 w/w %, hydroxyethylcellulose 1.0 w/w %, polyvinylpyrrolidone 1.5 w/w %, disodium EDTA 0.5 w/w %, allantoin 0.6 w/w %, DL-panthenol 1.0 w/w %, propylene glycol 0.2 w/w %, polysorbate 0.1 w/w %, glycerin 12 w/w %, purified water 69.9 w/w %, buffered with 0.1 M triethanolamine to pH 6.15.

Example 3

An embodiment of the present invention was compounded as described to determine materials compatibility and range of material usage.

Silver citrate salt 36 ppm, Aloe vera acemannan 0.15 w/w %, Carboxymethylcellulose 1.75 w/w %, polyvinylpyrrolidone 1.5 w/w %, disodium EDTA 0.5 w/w %, allantoin 0.6 w/w %, DL-panthenol 1 w/w %, propylene glycol 0.2 w/w %, glycerin 15 w/w %, purified water 53.3%, buffered with 0.1M triethanolamine to pH 5.7.

Example 4

An embodiment of the present invention was compounded as described to determine materials compatibility and range of material usage.

Silver citrate salt 50 ppm, Aloe vera acemannan 0.15 w/w %, hydroxyethylcellulose 1.0 w/w %, polyvinylpyrrolidone 3.0 w/w %, disodium EDTA 0.6 w/w %, allantoin 1.5 w/w %, DL-panthenol 1.0 w/w %, propylene glycol 0.2 w/w %, glycerin 15 w/w %, purified water 35.4 w/w %, buffered with 0.1 M triethanolamine to pH 5.8.

Example 5

An embodiment of the present invention was compounded as described to determine materials compatibility and range of material usage.

Silver citrate salt 75 ppm, Aloe vera acemannan 0.15 w/w %, hydroxyethylcellulose 1.0 w/w %, polyvinylpyrrolidone 1.5 w/w %, disodium EDTA 0.5 w/w %, DL-panthenol 1.0 w/w %, propylene glycol 0.2 w/w %, glycerin 15 w/w %, purified water 53.3 w/w %, buffered with 0.1 M sodium hydroxide to pH 6.2.

Example 6

An embodiment of the present invention was compounded as described to determine materials compatibility and range of material usage.

Silver benzoate salt 100 ppm, Aloe vera acemannan 0.15 w/w %, hydroxyethylcellulose 1.0 w/w %, polyvinylpyrrolidone 1.5 w/w %, disodium EDTA 0.5 w/w %, allantoin 0.6 w/w %, DL-panthenol 1.0 w/w %, propylene glycol 0.2 w/w %, polysorbate 0.1 w/w %, glycerin 12 w/w %, purified water 70.0 w/w %, buffered with 0.1 M triethanolamine to pH 6.35.

Example 7

An embodiment of the present invention was compounded as described to determine materials compatibility and range of material usage.

Silver nitrate salt 1000 ppm, Aloe vera acemannan 0.15 w/w %, hydroxyethylcellulose 1.0 w/w %, polyvinylpyrrolidone 1.5 w/w %, disodium EDTA 0.5 w/w %, allantoin 0.6 w/w %, DL-panthenol 1.0 w/w %, propylene glycol 0.2 w/w %, polysorbate 0.1 w/w %, glycerin 12 w/w %, purified water 70.0 w/w %, buffered with 0.1 M triethanolamine to pH 5.99.

Example 8

The antimicrobial activity of silver citrate (SC) in USP Purified Water and silver antimicrobial hydrogel (SC-Gel), described herein in Example 2, was tested using the microtube dilution method for determining minimal inhibitory concentrations (MIC) listed in the chart below. In brief, a standard inoculum (100 μL of a 1:200 dilution of a 0.5 MacFarland turbidity standard) of each microorganism was prepared in standard growth media and added to equal volumes of two-fold serial dilutions of SC and SC-Gel. MICs were determined visually as the highest dilution of SC, or SC-Gel, that inhibited growth after incubating the mixtures overnight at 35° C., except for *Candida albicans*, which required 48 hrs incubation. Mixtures demonstrating no growth remained clear while mixtures exhibiting growth turned cloudy. The MIC dilution was converted to μg/mL by multiplying the neat drug ($Ag^+$) concentration by the dilution appropriate dilution factor.

This example demonstrates that the composition of the SC-Gel outperform SC alone in the diverse selection of microorganisms tested.

| Microorganism | ATCC # | Type | SC Gel MIC (SD) | SC Liquid MIC (SD) | N |
| --- | --- | --- | --- | --- | --- |
| *Acinetobacter baumanni* | 15308 | GNR | 0.29 (0.20) | 1.90 (0.99) | 11 |
| *Bacillus anthracis Sterne* | Colorado Dept of Public Health and Environment | GPR | 0.47 (0.00) | 1.88 (0.00) | 3 |
| *Candida albicans* | 10231 | Yeast | 0.15 (0.06) | 3.01 (3.22) | 11 |
| *Escherichia coli* | 25922 | GNR | 0.34 (0.15) | 1.59 (0.43) | 11 |
| *Enterococcus faecalis* | 29212 | GPC | 0.98 (0.73) | 6.88 (0.68) | 11 |

-continued

| Microorganism | ATCC # | Type | SC Gel MIC (SD) | SC Liquid MIC (SD) | N |
|---|---|---|---|---|---|
| *Pseudomonas aeruginosa* | 27853 | GNR | 0.83 (1.18) | 2.30 (1.22) | 11 |
| *Staphylococcus aureus* | 6538 | GPC | 0.17 (0.07) | 5.62 (2.60) | 11 |
| *Staphylococcus epidermidis* | 29887 | GPC | 0.17 (0.07) | 1.29 (0.67) | 11 |
| *Staphylococcus pyogenes* | 19615 | GPC | 0.10 (0.00) | 1.04 (0.45) | 3 |

ATCC = American Type Culture Collection, Manassas, VA
GNR = gram negative rod;
GPC = gram positive cocci;
GPR = gram positive rods;
MIC = Minimal inhibitory concentration (□g/mL);
N = number of replicates;
SC = silver citrate;
SD = standard deviation Example 9

The antimicrobial activity of silver antimicrobial hydrogel (SC-Gel), described herein in Example 2, was compared against two currently marketed drugs (miconazole/MIC and silver sulfadiazine/SSD) in a small group of diverse microorganisms: *Candida albicans* (yeast); *Pseudomonas aeruginosa* (gram negative bacterium), *Staphylococcus aureus* (gram positive bacterium), and *Trichomonas vaginalis* (protozoan). *Trichomonas vaginalis* was tested as described in the next paragraph, and the bacteria and yeast were tested using the microtube dilution method for MIC determination. In brief, a standard inoculum (100 µL of a 1:200 dilution of a 0.5 MacFarland turbidity standard) of each microorganism was prepared in standard growth media and added to equal volumes of two-fold serial dilutions of SC and SC-Gel. MICs were determined visually as the highest dilution of SC, or SC-Gel, that inhibited growth after incubating the mixtures overnight at 35° C., except for *C. albicans*, which required 48 hrs incubation. Mixtures demonstrating no growth remained clear while mixtures exhibiting growth turned cloudy. The MIC dilution was converted to µg/mL by multiplying the neat drug ($Ag^+$) concentration by the dilution appropriate dilution factor.

*Trichomonas vaginalis* was purchased from BioMed Diagnostics Inc, White City, Oreg. and subcultured per the manufacturer instructions in InPouch™ TVC Subculture Medium. On the day of subculturing, 50 µL of *T. vaginalis* live culture was added to 250 µL of a 50:50 mixture of SC-Gel and InPouch™ TVC Subculture Medium (test), as well as a 50:50 mixture of sterile deionized water and InPouch™ TVC Subculture Medium (control). After 4 days incubation at 30° C., 50 µL of test and control solution were viewed under 400× microscopically. SC-Gel test mixture revealed 0-1 non-motile *T. vaginalis* organisms/microscopic field, and the control mixture revealed 3-4 motile *T. vaginalis* organisms/microscopic field. These data suggest SC-Gel inhibits or kills *T. vaginalis* at the concentration tested (7.5 µg/mL).

This example demonstrates that the constituents of the SC-Gel appear to have equal too or greater potency than silver sulfadiazine in inhibiting the growth of tested strains of *Pseudomonas aeruginosa* and *Staphylococcus aureus*, and demonstrates that it has greater inhibitory properties against *Candida albicans* than Miconazole as well as having inhibitory properties against *Trichomonas vaginalis*. In-toto, these data suggest SC-Gel exhibits a very broad antimicrobial range, covering bacteria (gram positive and gram negative), yeast, and protozoans.

| Microorganism | ATCC | SC Gel (SD) | MZL (SD) | SSD (SD) |
|---|---|---|---|---|
| *Candida albicans* | 10231 | 0.16 (0.06) N = 9 | 0.49 (0.17) N = 3 | N/A |
| *Pseudomonas aeruginosa* | 27853 | 1.56 (1.69) N = 6 | N/A | 2.36 (0.94) N = 4 |
| *Staphylococcus aureus* | 6538 | 0.47 (0.00) N = 3 | N/A | 0.47 (0.00) N = 3 |

ATCC = American Type Culture Collection, Manassas, VA
MZL = Miconazole;
SC = silver citrate;
SSD = silver sulfadiazine;
SD = standard deviation;
N/A not applicable for organism tested Example 10

An eight-year old equine gelding suffered a severe substantial laceration to the right rear hock. The wound extended from right below the joint and was approximately 22.5 cm by 14 cm extending from the medial to the lateral side of the canon bone with the depth visually exposing the joint capsule. The horse was placed on systemic antibiotics for one week and a topical antimicrobial. The wound wasn't progressing in healing and the animal's topical primary dressing was changed to the silver antimicrobial hydrogel dressing described in Example 2. The wound was treated every other day and bandaged. Wound color rapidly improved with enhanced granulation formation and wound shrinkage was observed within 7 days of initiation of therapy. Treatments have progressed with wound improvement over an eight-week period. The animal exhibited no pain from the administration of the dressing.

Example 11

A 42 year old female Caucasian presented with a first-degree burn to the forearm. The patient was treated with the silver antimicrobial hydrogel described in Example 2. The patient applied the composition without a secondary dressing three to four times per day for two days. Prior to application of the hydrogel pain was assessed using the Pain Quality Assessment Scale (PQAS); results are as follows: hot scored 1, cold scored 4, sensitivity to touch scored 2, and surface pain scored 2. After application of the hydrogel, pain was reassessed using the PQAS, results are as follows: hot scored 0, cold scored 0, sensitivity to touch scored 0, and surface pain scored 0. Upon application of the composition pain subsided within less than one minute. After two days the signs and symptoms had abated.

Example 12

A 57 year old male Caucasian presented with herpes labialis, commonly known as a fever blister. The patient reported a history of recurrent episodes of herpes labialis outbreaks. The silver antimicrobial hydrogel described in Example 2 was applied to the patient's lesion approximately four times a day as needed based on onset of a painful muco-cutaneous sensation. Complete loss of pain sensation was experienced within less than one minute after application of the antimicrobial hydrogel. No signs and symptoms of the herpes labialis infection were observed after three days of treatment with the composition.

Example 13

An embodiment of the present invention was compounded as described above to determine compatibility and acceptability of use or absence of use of a range of tetraacetic acids as discussed above. The composition of Example 2 was utilized (SC=silver citrate, ACM=acemannan) for evaluation by either removing or replacing disodium EDTA with an alternate tetraacetic acid as listed: (1) tetrasodium ethylenediaminetetraacetic acid (EDTA Tetrasodium), (2) 1,2-bis(o-aminophenoxy) ethane-N,N,N',N'-tetraacetic (BAPTA), (3) 1,4,7,10-tetraazacyclododecane-1,4,7,10-tetraacetic acid (DOTA), (4) ethylene glycol tetraacetic acid (EGTA), or (5) no EDTA.

The method described in Example 8 for minimum inhibitory concentration (MIC) was utilized for evaluation of activity of the compositions against *Staphylococcus aureus* and *Streptococcus pyogenes* (Gram-positive cocci) and *Pseudomonas aeruginosa* and *Escherichia coli* (Gram-negative rod) organisms.

TABLE

| Minimal Inhibitory Concentration (MIC) µg/ml | | | | | | |
|---|---|---|---|---|---|---|
| Organism | ATCC | SC control | SC/ACM gel with EDTA Tetrasodium | SC/ACM gel with BAPTA | SC/ACM gel with DOTA | SC/ACM gel with EGTA | SC/ACM gel no EDTA |
| S. aureus | 6538 | +/−15[1] | 0.440 | +/−7.5[1] | 5.625 | 2.813 | ND7.5[3] |
| n = 12 | | n = 12 | n = 24 | n = 12 | n = 12 | n = 12 | n = 12 |
| (SD) | | | (0.083) | | (2.165) | (1.083) | |
| S. pyogenes | 19615 | ND15[2] | 0.938 | +/−7.5[1] | 5.625 | +/−7.5[1] | +/−7.5[1] |
| (SD) | | n = 6 | n = 6 | n = 6 | n = 6 | n = 6 | n = 6 |
| | | | (0.00) | | (2.652) | | |
| P. aeruginosa | 27853 | 11.25 | 1.289 | ND7.5[3] | ND7.5[3] | 5.625 | ND7.5[3] |
| (SD) | | n = 12 | n = 24 | n = 12 | n = 12 | n = 12 | n = 12 |
| | | (4.33) | (0.651) | | | (2.165) | |
| E. coli | 25922 | 7.5 | 1.875 | ND7.5[3] | ND7.5[3] | 0.469 | +/−7.5[1] |
| (SD) | | n = 6 | n = 6 | n = 6 | n = 6 | n = 6 | n = 6 |
| | | (0.00) | (0.00) | | | (0.00) | |

ATCC = American Type Culture Collection
SD = standard deviation
[1]+/−Partial killing with inhibition at highest level tested (7.5 µg/ml for tetraacetic acid gels) (15 µg/ml for SC control)
[2]ND15—No activity detected at 15 µg/ml highest level tested
[3]ND7.5—No activity detected at 7.5 µg/ml highest level tested The compositions containing tetrasodium EDTA and EGTA had a synergistic effect against both gram-positive and gram-negative organisms evaluated as compared to the silver citrate control. Compositions containing DOTA and BAPTA improved activity compared to the control but observed improvement was limited to gram-positive cocci tested, *S. aureus* and *S. pyogenes*. In addition, the silver citrate/acemannan composition absent of a tetraacetic acid also outperformed the silver citrate control in its effect on growth of *S. pyogenes*. Therefore these data suggest, dependent on the organism of interest, compositions of a silver salt and acemannan with or without a tetraacetic acid is superior to a silver salt alone. It also suggests that differences exist between tetraacetic acids as a composition stabilizer choice.

REFERENCES CITED

The following documents and publications are hereby incorporated by reference.

Related U.S. Patent Documents

| | | |
|---|---|---|
| 4,735,935 | April 1988 | McAnalley |
| 4,851,224 | July 1989 | McAnalley |
| 4,966,892 | October 1990 | McAnalley |
| 4,959,214 | September 1990 | McAnalley |
| 4,957,907 | September 1990 | McAnalley |
| 4,917,890 | April 1990 | McAnalley |
| 5,118,673 | June 1992 | Carpenter |
| 5,106,616 | April 1992 | McAnalley |
| 5,308,838 | May 1994 | McAnalley |
| 5,441,943 | August 1995 | McAnalley |
| 5,487,899 | January 1996 | Davis |
| 5,703,060 | December 1997 | McAnalley et al. |
| 5,760,102 | June 1998 | Hall |
| 5,902,600 | May 1999 | Woller, et al. |
| 5,902,796 | May 1999 | Shand et al. |
| 6,274,548 | August 2001 | Ni et al. |

-continued

| | | |
|---|---|---|
| 6,436,679 | August 2002 | Qiu et al. |
| 7,196,072 | March 2007 | Pasco et al. |
| 7,553,805 | June 2009 | Tichy et al. |
| 7,732,486 | June 2010 | Arata b |
| 7,842,317 | November 2010 | Kiani |
| 7,863,264 | January 2011 | Vange, et al. |

Foreign Patent Documents

| | | |
|---|---|---|
| US 2008152697 | February 2002 | US |
| WO 2006015317 | July 2004 | WO |
| GB 2028130 | March 1980 | GB |
| CA 1216520 | January 1987 | CA |

| | -continued | |
|---|---|---|
| RU 2317811 | February 2008 | RU |
| WO 03090799 | November 2003 | WO |

OTHER PUBLICATIONS

Atiyeh B S, Costagliola M, Hayek S N, Dibo S A. Effect of silver on burn wound infection control and healing: Review of the literature, Burns 33; 2007: 139-148

Azghani A O, Williams I, Holiday D B, Johnson A R. A beta-linked mannan inhibits adherence of Pseudomonas aeruginosa to human lung epithelial cells. Glycobiology. 1995 February; 5(1): 39-44

Becker L C, Bergfeld W F, Belsito D V, Klaassen C D, Marks J G, Shank R C, Slaga T J, Snyder P W, and Andersen F A. Final report of the safety assessment of allantoin and its related complexes. International Journal of Toxicology: 29 (Supplement 2); 2010: 84S-97S Bouwstra J A, Groenink W W, Kempenaar J A, Romeijn S G, and Ponec M. Water distribution and natural moisturizer factor content in human skin equivalents are regulated by environmental relative humidity. Journal of Investigative Dermatology: Vol 128; 2008: 378-388

Brown M R W, Winsley B E. Effect of polysorbate 80 on cell leakage and viability of Pseudomonas aeruginosa exposed to rapid changes of pH, temperature and tonicity. J. Gen. Microbiol; 56; 1969: 99-207

Castellano J. J., Shafii S. M., Ko F., Donate G, Wright T. E., Mannari R. J., Payne W. G., Smith D. J., Robson M. C. Comparative evaluation of silver-containing antimicrobial dressings and drugs. International Wound Journal: 4; 2007: 114-122

CDC Worker Health Chartbook 2004, www.cdc.govniosh/docs/2004-146/ch2/ch2-7-4.asp.htm.

Chang T. & Weinstein L., In vitro activity of Silver Sulfadiazine against Herpes virus hominis. Journal of Infectious Disease: Vol 132, No 1; July 1975: 79-81

Desai M. H., Rutan R. L., Heggers J. P., Herndon D. N. Candida infection with and without nystatin prophylaxis, an 11-year experience with patients with burn injury. Arch Surg, Vol 127; February 1992: 159-162

Djokic S., Synthesis and antimicrobial activity of silver citrate complexes. Bioinorganic Chemistry and Applications: Article ID 436458; Vol 2008: 1-7

Drake P. & Hazelwood K., Exposure-related health effects of silver and silver compounds: a review. Oxford University Press, Vol 49. No 7. 2005: 575-585

Fan, K, Tang, J., Escandon, J., Kirsner, R. S., State of the art in topical wound-healing products. Journal of Plastic and Reconstructive Surgery. 127 (Suppl.); 2011: 44S-59S Ferri: Ferri's Clinical Advisor 2011, 1st ed., Mosby, Elsevier Press; 2010

Glasser J S, Guymon C H, Mende K, Wolf S E, Hospenthal D R, and Murray C K. Activity of topical antimicrobial agents against multidrug-resistant bacteria recovered from burn patients. Burns 36; 2010: 1172-1184

Goodman and Gilman's The Pharmacologic Basis of Therapeutics, Brunton, Lawrence L., Lazo, John S., Parker, Keith L., 11$^{th}$ Ed; 2006: 1105-1109

Hamilton-Miller J. M. T. & Shah S. A microbiological assessment of silver fusidate, a novel topical antimicrobial agent. Int J Antimicrobial Agents: 7; 1996: 97-99

Jacobsen F, Fisahn, C, Sorkin, M, Thiele I, Hirsch T, Stricker I, Klaasen T, Roemer A, Fugmann B, Steinstraesser L. Efficacy of topical delivered Moxifloxacin against MRSA and Pseudomonas aeruginosa wound infection. Antimicrobial Agents Chemotherapy, doi: 10.1128/AAC.01071-10, AAC, American Society for Microbiology, 22 Feb. 2011

Jettanacheawchankit S, Sasithanasate S, Sangvanich P, Banlunara W, and Thunyakitpisal P. Acemannan stimulates gingival fibroblast proliferation; expressions of keratinocyte growth factor-1, vascular endothelial growth factor and type I collagen; and wound healing. J. Pharmacol Sci: 109; 2009: 525-531

Karlsmark, T, Agerslev R H, Bendz S H, Larsen Jr, Roed-Petersxen J, Andersen K E. Clinical performance of a new silver dressing, Contreet Foam, for chronic exuding venous leg ulcers. Journal of Wound Care: Vol. 12, No. 9; 2003: 351-354

Kaur P, Vadehra D V. Effect of certain chelating agents on the antibacterial action of silver nitrate. J Hyg Epidemiol Microbiol Immunol: 32(3); 1988: 299-306

Khorasani G, Hosseinmehr S J, Azadbakht M, Zamani A, Mandavi M R. Aloe Versus Silver Sulfadiazine Creams for second-degree burns: a randomized controlled study. Surg Today: 39; 2009: 587-591

Kobayashi D, Kusama M, Onda M, and Nakahata N. The effect of pantothenic acid deficiency on keratinocyte proliferation and the synthesis of keratinocyte growth factor and collagen in fibroblasts. J Pharmacol Sci: 115; 2011: 230-234

Krizek T J, Robson M C. Evolution of quantitative bacteriology in wound management. Am J Surg: 130; 1975: 579-584

Lansdown, A B G. A pharmacological and toxicological profile of silver as an antimicrobial agent in medical devices. Advances in Pharmacological Sciences: ID 910686; Volume 2010: 1-16

Latenser, B. A., Burn Treatment Guidelines, Bope: Conn's Current Therapy 2011, 1$^{st}$ Ed.

Lee J H, Chae J D, Kim D G, Hong S H, Lee W M, and Ki M. Staphylococcus aureus. Korean J Lab Med: 30; 2010: 20-7

Loh J. et al., Silver resistance in MRSA isolated form wound and nasal sources in humans and animals. Int Wound J: 6; 2009: 32-38

Manuo S, Saekl T. Femtosecond laser direct writing of metallic microstructures by photo-reduction of silver nitrate in a polymer matrix. Opt Express: 16(2); 2008 Jan. 21: 1174-1179

Martin L K. Wound microbiology and the use of antibacterial agents. In: Falabella A F, Kirstner R S, eds. Wound Healing. Boca Raton, Fla.: Taylor and Francis Group; 2005: 83-101

Mandell: Mandell, Douglas, and Bennett's Principles and Practice of Infectious Diseases. 7th ed.; Churchill Livingstone, Elsevier Press; 2009:1-4

Panacek A, Kolar M, Vecerova R, Prucek R, Soukupova J, Krystof V, Hamal P, Zboril R, and Kvitek L. Antifungal activity of silver nanoparticles against Candida spp. Biomaterials: 30; 2009: 6333-6340

Poor M R, Hall J E, Poor A S. Reduction in the incidence of alveolar osteitis in patients treated with the SaliCept patch, containing acemannan hydrogel. J Oral Maxillofac Surg: 60(4); 2002 April: 374-379

Rai M, Yadav A, Gade A. Silver nanoparticles as a new generation of antimicrobials. Biotechnology Advances: 27; 2009: 76-83

Remington, The Science and Practice of Pharmacy. 21$^{st}$ Edition, Part 5; 2006: 1080

Remington, The Science and Practice of Pharmacy. 21st Edition, Part 7; 2006: 1290

Report of Data From 1999-2008. American Burn Association, National Burn Repository, version 5, 2009

Reynolds T, *Aloes, The genus Aloe*. Medicinal and Aromatic Plants-Industrial Profiles. CRC Press, 2004. Chapt 9-11

Roberts D B, Travis E 1. Acemannan-containing wound dressing gel reduces radiation-induced skin reactions in C3H mice. Int J Radiat Oncol Biol Phys: 32(4); 1995 Jul. 15: 1047-1052

Robson M C. Wound infection a failure of wound healing caused by an imbalance of bacteria. Surgical Clinics of North America: Vol 77, Isse 3; Jun. 4, 1997: 637-650

Shimizu F., et al. Specific inactivation of Herpes Simplex Virus by silver nitrate at low concentrations and biological activities of the inactivated virus. Antimicrobial Agents and Chemotherapy; July 1976: 57-63

Toxicology of Disodium EDTA. National Library of Medicine, Toxicology Data Network http://toxnet.nlm.nih.gov/cgi-bin/sis/search/f?./temp/~I6Z04s:1 http://www.ameriburn.org/resources_factsheet.php

What is claimed is:

1. An antimicrobial hydrogel comprising:
   (a) a soluble silver salt, wherein the soluble silver salt is anhydrous or hydrous stabilized having a concentration of ionic silver in the range of 0.01-100 ppm;
   (b) acemannan, wherein the acemannan has a concentration of 0.01 to 1.0 w/w %; and
   (c) a stabilizing chelating agent, wherein the stabilizing chelating agent has a concentration of 0.01 to 5.0 w/w %, wherein the stabilizing chelating agent is EDTA, ethylene glycol tetraacetic acid (EGTA), or mixtures thereof.

2. The antimicrobial hydrogel of claim 1, wherein the stabilizing chelating agent is in its salt form.

3. The antimicrobial hydrogel of claim 1, wherein the silver salt is selected from the group consisting of silver citrate, silver dihydrogen citrate, silver chloride, silver acetate, silver nitrate, silver fusidate, silver benzoate, silver gluconate, and silver galacturonate.

4. The antimicrobial hydrogel of claim 1, wherein the acemannan is in an anhydrous form, and wherein the acemannan was separated using an alcohol precipitation method, a column purification method or an ultrafiltration method in an aqueous vehicle.

5. The antimicrobial hydrogel of claim 1, further comprising polyvinylpyrrolidone.

6. The antimicrobial hydrogel of claim 5, wherein the polyvinylpyrrolidone is in the concentration of 0.1 to 5.0 w/w %.

7. The antimicrobial hydrogel of claim 1, further comprising a sorbitan ester.

8. The antimicrobial hydrogel of claim 7, wherein the sorbitan ester is polysorbate.

9. The antimicrobial hydrogel of claim 8, wherein the concentration of polysorbate is 0.01-0.2 w/w %.

10. The antimicrobial hydrogel of claim 1, further comprising allantoin.

11. The antimicrobial hydrogel of claim 10, wherein the concentration of allantoin is 0.0001-2.0 w/w %.

12. The antimicrobial hydrogel of claim 1, further comprising a humectant, wherein the humectant is panthenol.

13. The antimicrobial hydrogel of claim 12, wherein panthenol is in the concentration of 0.1-3.0 w/w %.

14. The antimicrobial hydrogel of claim 1, further comprising a humectant, wherein the humectant is propylene glycol.

15. The antimicrobial hydrogel of claim 14, wherein propylene glycol is in the concentration of 0.01-1.0 w/w %.

16. The antimicrobial hydrogel of claim 1, further comprising a humectant.

17. The antimicrobial hydrogel of claim 1, further comprising a non-ionic water soluble polymer.

18. The antimicrobial hydrogel of claim 17, wherein the non-ionic water soluble polymer is hydroxyethylcellulose.

19. The antimicrobial hydrogel of claim 17, wherein the non-ionic water soluble polymer is carboxymethylcellulose.

20. The antimicrobial hydrogel of claim 17, wherein the non-ionic water soluble polymer is hydroxypropylcellulose.

21. The antimicrobial hydrogel of claim 17, wherein the concentration of non-ionic water soluble polymer is 0.01-5.0 w/w %.

22. The antimicrobial hydrogel of claim 1, wherein the antimicrobial hydrogel is buffered to a pH of 4-7.4.

23. A method of treating bacteria infected wounds or lesions or burns in a subject, comprising topically administering to the subject an effective amount of the antimicrobial hydrogel of claim 1.

24. A method of treating bacteria infected wounds or lesions or burns in a subject, comprising topically administering to the subject an effective amount of the antimicrobial hydrogel of claim 17.

25. A method of treating a wound or lesion or burn in a subject, comprising topically administering to the subject an effective amount of the antimicrobial hydrogel of claim 1, wherein the therapeutic composition will create a physiologic environment for accelerated wound healing.

26. A method of treating a wound or lesion or burn in a subject, comprising topically administering to the subject an effective amount of the antimicrobial hydrogel of claim 1 that relieves pain.

27. A method of treating a wound or lesion or burn in a subject, comprising topically administering to the subject an effective amount of the antimicrobial hydrogel of claim 1 that will absorb or donate moisture for physiologic healing of the wound or lesion or burn.

28. The antimicrobial hydrogel of claim 1, wherein the antimicrobial hydrogel has activity against *E. coli, P. aeruginosa*, and *S. aureus*.

* * * * *